(12) United States Patent
Klaffenboeck et al.

(10) Patent No.: US 8,828,048 B2
(45) Date of Patent: Sep. 9, 2014

(54) MEDICAL INSTRUMENT

(76) Inventors: Johann Klaffenboeck, Strobl (AT); Lukas Klaffenboeck, Graz (AT)

( * ) Notice: Subject to any disclaimer, the term of this patent is extended or adjusted under 35 U.S.C. 154(b) by 85 days.

(21) Appl. No.: 13/138,993

(22) PCT Filed: May 14, 2010

(86) PCT No.: PCT/EP2010/056656
§ 371 (c)(1),
(2), (4) Date: Dec. 29, 2011

(87) PCT Pub. No.: WO2010/130829
PCT Pub. Date: Nov. 18, 2010

(65) Prior Publication Data
US 2012/0101483 A1 Apr. 26, 2012

(30) Foreign Application Priority Data
May 15, 2009 (AT) .................................. A 764/2009

(51) Int. Cl.
*A61B 17/00* (2006.01)
*A61B 17/068* (2006.01)
*A61B 17/29* (2006.01)
*A61B 17/064* (2006.01)

(52) U.S. Cl.
CPC ....... *A61B 17/068* (2013.01); *A61B 2017/2926* (2013.01); *A61B 17/00234* (2013.01); *A61B 2017/00539* (2013.01); *A61B 17/0643* (2013.01)
USPC ........................................................ 606/206

(58) Field of Classification Search
USPC ................. 606/1, 51–52, 205–209, 213, 216, 606/218–220, 166–167, 107, 139–150; 227/175.1–182.1; 600/562–571, 104; 173/9, 177, 200, 168–169, 141, 144, 173/149, 152; 294/213
See application file for complete search history.

(56) References Cited

U.S. PATENT DOCUMENTS 4,449,550 A * 5/1984 Ranalli .................... 137/624.13
4,485,817 A 12/1984 Swiggett
(Continued)

FOREIGN PATENT DOCUMENTS

DE 102006052086 5/2008

OTHER PUBLICATIONS

English Abstract of DE102006052086.

*Primary Examiner* — David Eastwood
(74) *Attorney, Agent, or Firm* — Dykema Gossett PLLC (57) ABSTRACT

The invention relates to a medical instrument comprising an elongated element, which is preferably configured for transoral placement in a stomach, and an end effector (100) arranged at one end of the elongated element, wherein the end effector (100) can be operated by means of a hydraulic operating mechanism (1), wherein the hydraulic operating mechanism (1) comprises a cylinder (20) having at least one, preferably two, three, four, or five, overflow channels (21*a*, 21*b*, 21*c*, 21*d*) for a hydraulic fluid, which are connected to the cylinder interior by means of at least one bore (22, 22*b*, 22*b'*, 22*c*, 22*c'*, 22*d*, 22*d'*), a piston (30) arranged in the cylinder (20) and movable along the longitudinal axis of the cylinder (20) is provided, wherein the piston (30) divides the interior (23) of the cylinder (20) into a first cylinder chamber (23*a*) and a second cylinder chamber (23*b*) and is connected to the end effector (100) by means of a piston rod (31), and at least one connection (41) for introducing hydraulic fluid into the first cylinder chamber (23*a*) and at least one further connection (41*a*, 41*b*, 41*c*, 41*d*), which is connected to at least one overflow channel (21*a*, 21*b*, 21*c*, 21*d*) of the cylinder (20), are provided.

8 Claims, 7 Drawing Sheets

(56) References Cited

U.S. PATENT DOCUMENTS

| | | |
|---|---|---|
| 4,962,751 A | 10/1990 | Krauter |
| 5,361,583 A | 11/1994 | Huitema |
| 5,577,992 A | 11/1996 | Chiba et al. |
| 7,801,037 B2 | 9/2010 | Wang |
| 2002/0111604 A1* | 8/2002 | Doyle et al. ............ 606/1 |
| 2004/0059349 A1 | 3/2004 | Sixto et al. |
| 2005/0245913 A1* | 11/2005 | Del Rio ............... 606/1 |
| 2007/0213769 A1* | 9/2007 | Schulz et al. ........ 606/219 |

* cited by examiner

MEDICAL INSTRUMENT

BACKGROUND OF THE INVENTION

1. Field of the Invention

The invention relates to a medical instrument which includes an elongated element preferably configured for transoral placement in a patient's stomach, and an end effector which can be positioned at one end of the elongated element and can be operated by means of a hydraulic actuating mechanism. The invention also relates to a method of operating the end effector which is attached in particular at one end of an endoscopic system.

2. The Prior Art

DE 44 35 644 B1 describes a hydraulic bending mechanism for a bending section of an endoscopic system. A similar device can also be found in EP 0 401 129 A1.

In U.S. Pat. No. 4,485,817 A there is disclosed a hydraulic bending mechanism for an end effector, where one piston is moved against a second piston to build up the pressure necessary in the hydraulic fluid for operating the end effector. Disadvantages of this hydraulic actuating mechanism are its complicated construction and the fact that this actuating mechanism can control only two defined operational states of the end effector. Stomach plication however will often require more than two operational states of the end effector, which makes the actuating mechanism unsuitable for such end effectors. A similar device is described in U.S. Pat. No. 5,361,583 A.

It is therefore the object of the present invention to provide a medical instrument with a hydraulic actuating mechanism which is simple in design and safe in operation and avoids the disadvantages of the state of the art.

SUMMARY OF THE INVENTION

The invention achieves this object by providing a medical instrument of the above-mentioned kind wherein the hydraulic actuating mechanism comprises a cylinder with at least one, preferably two, three, four or five, overflow passages for a hydraulic fluid which are connected to the interior of the cylinder by at least one bore, and where a piston movable along the longitudinal axis of the cylinder is provided in the cylinder, the piston partitioning the cylinder interior into a first cylinder space and a second cylinder space and connecting via a piston rod to the end effector, and where at least one fitting is provided for feeding hydraulic fluid into the first cylinder space and at least one further fitting is provided which is connected to at least one overflow passage of the cylinder.

In a first variant of the invention the overflow passages are configured as grooves on the outer wall of the cylinder and connect to the interior space of the cylinder by means of bores which are positioned at different distances from one end of the cylinder. Preferably, the cylinder is inserted into a sleeve, such that the overflow passages between the inner wall of the sleeve and the outer wall of the cylinder are formed by the grooves on the outer cylinder wall.

The fittings for the hydraulic fluid which connect to the interior space of the cylinder are preferably placed in a sealing element which is located at the end of the sleeve facing away from the piston rod, resulting in a compact and reliable hydraulic actuating mechanism.

In an alternative variant of the invention at least one overflow passage is located within the cylinder wall and connects to the cylinder space via at least one bore. While this variant will be more expensive to manufacture than the one above, it will not require a separate sealing element since the fittings for the hydraulic fluid are placed directly in the cylinder bottom. This will result in a smaller size of the instrument, which is important especially for endoscopic applications.

If hydraulic fluid is fed via the fitting connected to the adjacent first cylinder space, the piston moves forward away from the cylinder bottom and hydraulic fluid flows out of the second cylinder space via the second fitting, which is connected to the second cylinder space through an overflow passage. The volume of the first cylinder space increases while the volume of the second cylinder space decreases, and the piston rod of the piston is pressed out of the cylinder. When the at least one bore of the overflow passage is closed by the piston skirt of the piston in the cylinder, the piston can no longer move due to the counter-pressure in the second cylinder space and a defined position of the piston has been reached. This position of the piston corresponds to a defined operational state of the end effector connected to the piston rod. In accordance with the number and position of the overflow passages, respectively bores of the overflow passages, different operational states of the end effector connected to the medical instrument of the invention can be defined.

For controlling an end effector with two gripping elements as used in stomach plication, three operational states are required: a first closed state for positioning the end effector in the stomach of the patient, for instance; an opened state in which tissue is positioned between the gripping elements by moving these gripping elements against each other and finally a second closed state in which a staple device stitches together the tissue held between the gripping elements of the end effector. A suitable end effector may for instance be found in EP 2 187 559 A1 or in US 2004/59349 A1.

A preferred variant of the invention, which is particularly suitable for end effectors used in stomach plication, thus is provided with four overflow passages, three of which control the above-mentioned three operational states of the end effector, while the fourth overflow passage effects complete pressure relief in the second cylinder space.

Other end effectors may of course also be connected to the medical instrument of the invention; for such purposes a standardized adaptor element is preferably provided on the medical instrument. The end effectors connected to the hydraulic system of the invention may be diverse gripping elements, but also probes and other endoscopic and/or endosurgical elements.

To operate the hydraulic actuating mechanism of the invention a hydraulic aggregate is provided, which cooperates with the hydraulic actuating mechanism and comprises at least one pump and at least one hydraulic line leading to each fitting of the sealing element, each hydraulic line containing preferably at least one switching element.

Furthermore the object of the invention is achieved by an endosurgical instrument, especially an endoscope, comprising an elongated element which is preferably configured for transoral placement in the stomach, and an end effector placed at one end of the elongated element, which end effector is hydraulically actuated by means of the device according to the invention.

The end effector preferably has two claw-shaped gripping elements which can be moved from an open position to at least one, and preferably two or more, dosed position(s).

In a method according to the invention for actuating an end effector, in particular an end effector located at the tip of an endosurgical instrument, the position of a piston with a piston rod within a cylinder is changed with the use of a device according to the invention by the inflow of hydraulic fluid into a first cylinder space and/or the outflow of hydraulic fluid out of a second cylinder space, the piston position determining the operational state of the end effector which is connected to the piston rod.

Due to its space-saving design, the medical instrument of the invention can also be used with known endoscopic systems. The diameter of the medical instrument according to the invention can be kept small enough to place it in the channel of a state-of-the-art endoscope, for instance.

BRIEF DESCRIPTION OF THE DRAWINGS

The invention will be described in more detail below with reference to the enclosed drawings of variants, which are not to be interpreted as restrictive. There is shown in FIG. 1 an exploded view of the hydraulic actuating mechanism according to the invention;

FIG. 2b a second sectional view of the actuating mechanism rotated by 90° relative to the view of FIG. 2a;

FIG. 3b a side view of the actuating mechanism with end effector of FIG. 3a;

FIG. 3c an axonometric view of the actuating mechanism with end effector of FIG. 3a;

FIG. 7b an axonometric view of the end effector of FIG. 7a;

FIG. 7c a schematic hydraulic circuit for the end effector of FIG. 7a; and

DETAILED DESCRIPTION OF THE PREFERRED EMBODIMENT

Figure 1:
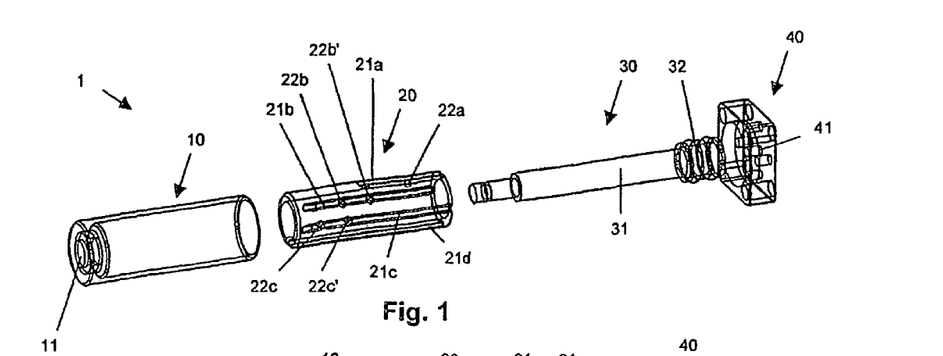

FIG. 1 shows in an exploded view the hydraulic actuating mechanism 1 of the invention, in particular for an endosurgical and/or endoscopic instrument. It has a sleeve 10 into which a cylinder 20 may be inserted. In the variant shown the cylinder 20 is provided with four overflow passages 21a, 21b, 21c, 21d, which are configured as grooves in the outer wall of the cylinder 20 in parallel with the longitudinal axis A of the cylinder and are connected to the interior 23 (FIGS. 2a, 2b) of the cylinder 20 via bores 22a, 22b, 22b', 22c, 22c', 22d, 22d'. Furthermore, the hydraulic actuating mechanism 1 comprises a piston 30 with a piston rod 31 and a sealing piston skirt 32, which can move in the cylinder 20 along its longitudinal axis A. Finally, there is provided a sealing element 40, which has five fittings 41, 41a, 41b, 41c, 41d, configured as bores for supplying hydraulic fluid through the sealing element 40.

Figure 2A:
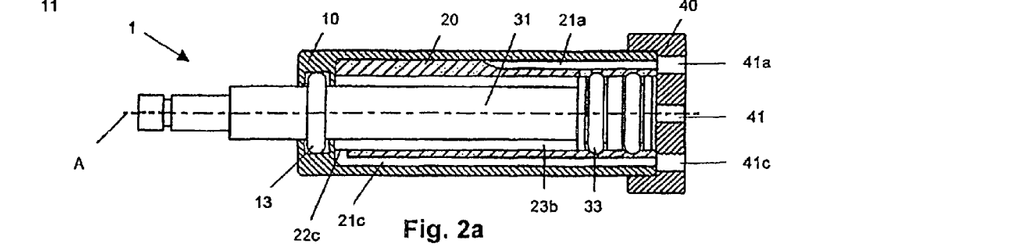
FIG. 2a a first sectional view of the actuating mechanism of FIG. 1 in the assembled state.
Figure 2B:
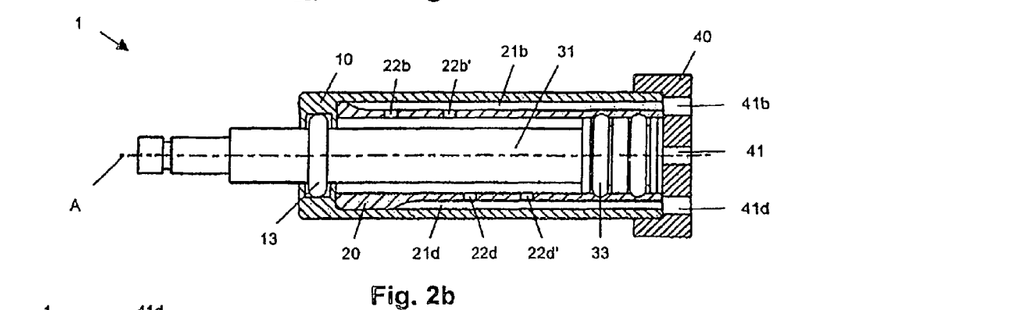

In FIGS. 2a and 2b the hydraulic actuating mechanism 1 is shown in its assembled state. The cylinder 20 sits in the sleeve 10 and is held in position by the sealing element 40. Sleeve 10, cylinder 20 and sealing element 40 are arranged relative to each other in such a way that the hydraulic fittings 41a, 41b, 41c, 41d, of the sealing element 40 are aligned to connect to the overflow passages 21a, 21b, 21c, 21d, said passages 21a, 21b, 21c, 21d, being connected via the bores 22a, 22b, 22b', 22c, 22c', 22d, 22d' to the interior of the cylinder 20.

The piston 30 is placed in the interior of the cylinder 20, its piston rod 31 being guided through a central opening 11 of the sleeve 10. On its piston skirt 32 within the cylinder 20 the piston 30 is provided with sealing means 33, which surround the piston skirt 32 in the form of rings and, when the piston 30 is in an appropriate position within the interior 23 of the cylinder 20, close at least one of the overflow passages 21a, 21b, 21c, 21d (FIG. 2a). Another sealing means 13 is provided in the concentric opening 11 of the sleeve 10 to prevent leaking of the hydraulic fluid from the cylinder 20.

Figure 2C:
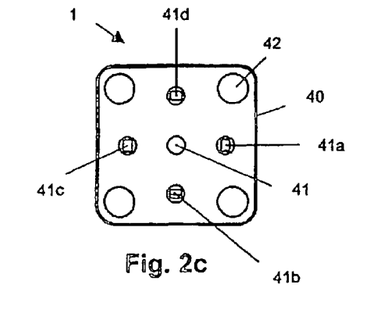
FIG. 2c a view of the actuating mechanism as seen from the side of the sealing element.
Figure 2D:
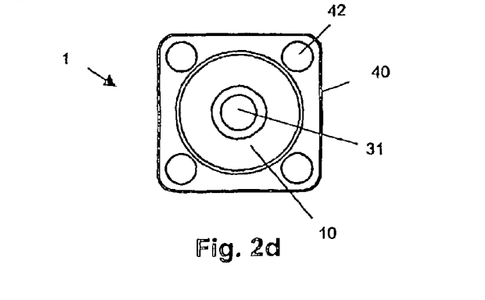
FIG. 2d a view of the actuating mechanism as seen from the side of the piston rod.

FIG. 2c is a view from above of the hydraulic actuating mechanism 1, where essentially the sealing element 40 is visible. One can see that, surrounding the central hydraulic fitting 41, four other fittings 41a, 41b, 41c, 41d are provided on the essentially square sealing element 40. In the corners of the sealing element 40 there are provided further openings 42, which receive fastening means (not shown) for attaching the sealing element 40 to the sleeve 10. FIG. 2d finally shows the hydraulic actuating mechanism 1 of the invention as seen when looking in the direction of the piston rod 31.

Figure 3A:
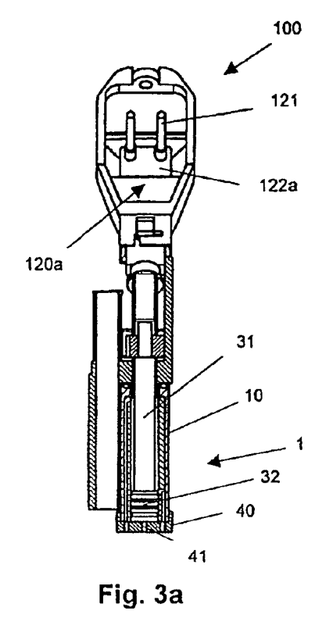
FIG. 3a a sectional view of the actuating mechanism with end effector.
Figure 3B:
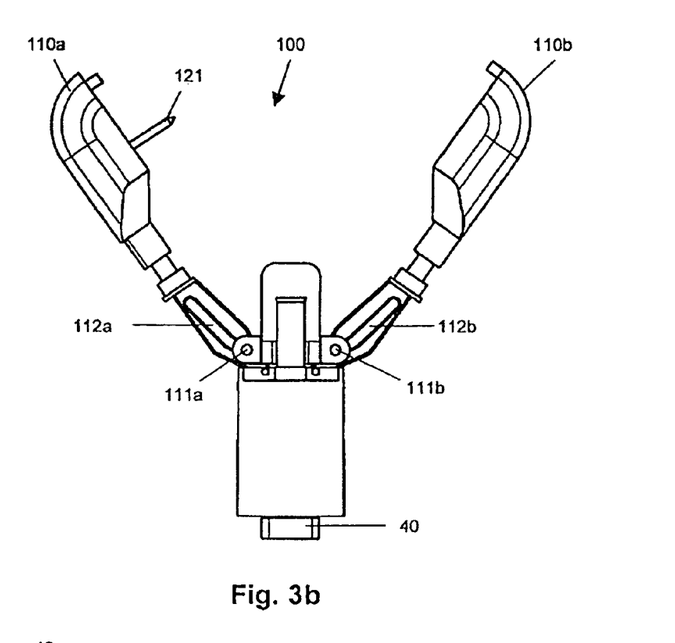
Figure 3C:
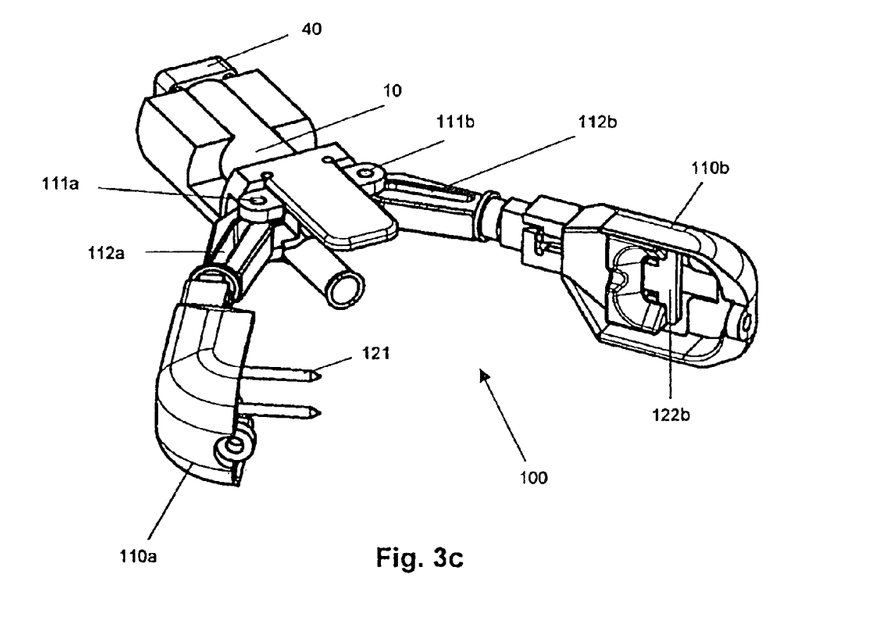

FIGS. 3a to 3c show the actuating mechanism 1 with an attached end effector 100, as used especially for endosurgery. FIG. 3a shows that the end effector 100 is positioned on the piston rod 31 of the piston 30, with the end effector 100 being in an "open" state as shown in FIG. 3b. The end effector 100 has two claw-like gripping elements 110a, 110b, the gripping element 110a carrying a first part 120a of a staple element, which comprises two pins 121 on a plate element 122a. A staple device of this kind is for instance disclosed in Austrian patent A 239/2009 of the applicant.

When the two gripping elements 110a; 110b of the end effector 100 are closed with the help of the hydraulic actuating mechanism 1 according to the invention, the first part 120a of the staple device meshes with the second part 122b of the staple device carried in the second gripping element 110b, for instance to fixate tissue in stomach plication. In order to be able to move the two gripping elements 110a, 110b towards each other or away from each other, guiding elements 111a, 111b are provided, which move along guiding grooves 112a, 112b when the piston 30 of the hydraulic actuating mechanism 1 is moved. In FIG. 3a the piston 30 is shown in its bottom position, where it essentially rests against the sealing plate 40. When the piston 30 is moved upwards by the hydraulic fluid entering through the central bore 41 of the sealing element 40, the guiding elements 111a, 111b are moved along the guiding grooves 112a in the direction towards the gripping elements 110a, 110b, thereby causing them to approach each other as required by the shape of the guiding grooves 112a, 112b. A curved shape of the guiding grooves 112a, 112b has the advantage that little force is necessary to reach a first closing position of the end effector 100, while in the second closing position the larger force required for breaking the pins 121 is provided due to the special shape of the guiding grooves 112a, 112b. Depending on the respective application the shape of the guiding grooves 112a, 112b may be chosen straight or curved.

The functioning of the hydraulic actuating mechanism 1 according to the invention will now explained in more detail. FIGS. 4a to 6d schematically present a hydraulic system 200 suitable for operating the hydraulic actuating mechanism 1. The hydraulic system 200 comprises a pump 201, which feeds hydraulic fluid to the hydraulic actuating mechanism 1, via a first hydraulic line 202 connected to a first cylinder space 23a. Furthermore, the overflow passages 21a, 21b, 21c, 21d are connected to other hydraulic lines 202a, 202b, 202c, 202d and are thus connected to a container 203 for hydraulic fluid. Each hydraulic line 202, 202a, 202b, 202c, 202d is provided with at least one switching element 204, for instance a hydraulic valve, permitting or inhibiting the flow of hydraulic fluid in the respective hydraulic line 202, 202a, 202b, 202c, 202d. In certain cases it is of advantage for the correct actuation of the end effector 100 to provide an additional restoring element 210, which is described in detail in FIGS. 8a and 8b.

Figure 4A:
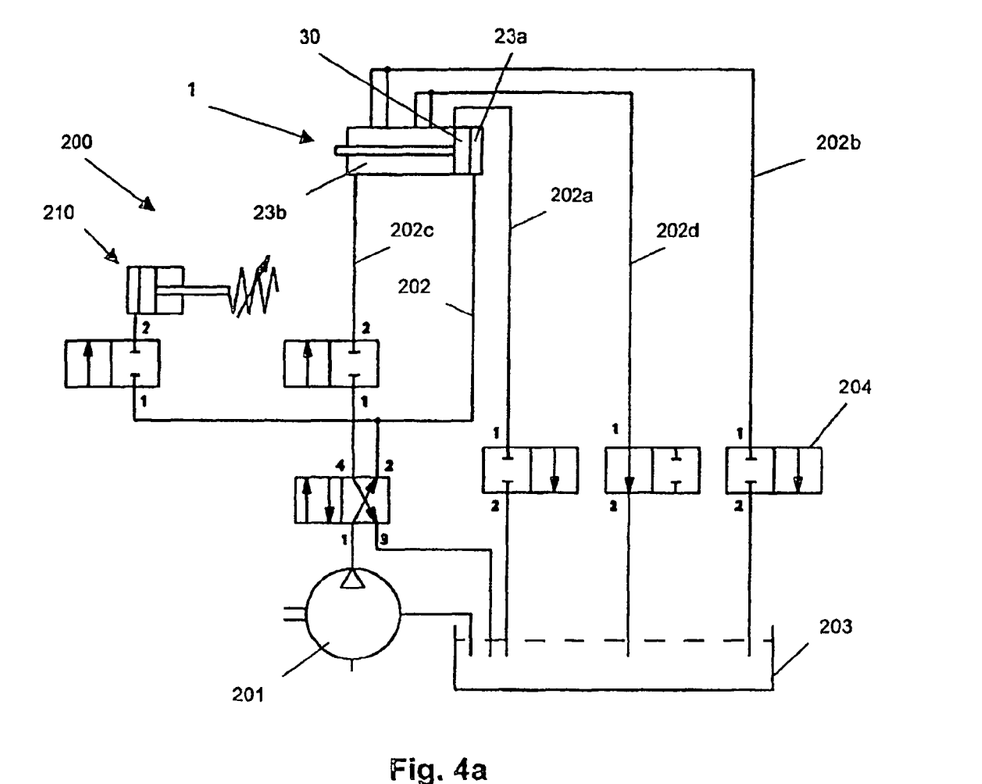
FIG. 4a a schematic hydraulic circuit for the opened end effector according to FIGS. 3a to 3c.
Figure 4B:
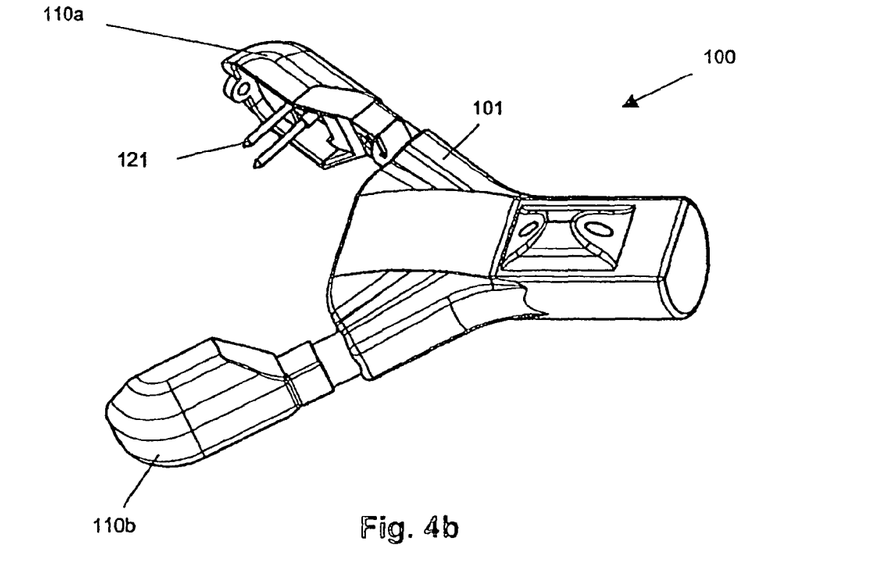
FIG. 4b the opened end effector of FIG. 3a with cover in an axonometric view.

FIG. 4a presents the switching state in which the piston 30 of the hydraulic actuating mechanism 1 is shown in its bottom position immediately adjacent to the sealing plate 40. Detailed presentation of the sealing plate 40 and the connected hydraulic lines is suppressed here to keep the drawing clear and uncluttered. The hydraulic lines 202, 202a, 202b, 202c, 202d are shown directly connected to points on the overflow passages 21, 21a, 21b, whereas they are actually connected to the fittings on the sealing plate 40, as shown in the variant of the invention of FIGS. 1 to 2d. The hydraulic scheme of FIG. 4a shows the state of the hydraulic system 200 in which the end effector is opened, as depicted in FIGS. 3a to 3c, respectively FIG. 4b. In FIG. 4b the end effector 100 of FIG. 3a is shown with its cover 101, for instance made of silicone.

The hydraulic actuating mechanism 1 is especially suitable for the operation of end effectors which are used in endoscopic stomach plication. In endoscopic stomach plication an end effector 100 is introduced into the stomach by means of an endoscope and subsequently actuated in such a way that a staple device contained in the end effector 100 (as for instance shown in FIGS. 3a to 3c) is placed in the (stomach) tissue. During the insertion of the endoscope into the stomach the end effector must be closed to avoid injury of the oesophagus or the stomach. On the other hand the end effector 100 must not be closed to such an extent that the pins 121 of the staple device lock with the second plate-shaped part 112b.

Figure 5A:
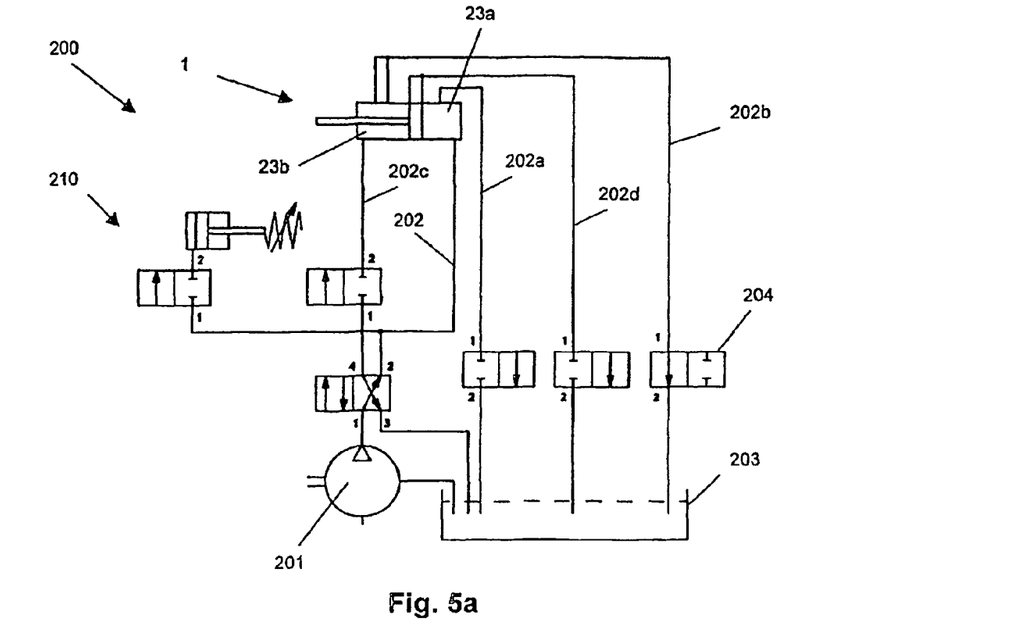
FIG. 5a a schematic hydraulic circuit for the end effector in a first closed state.
Figure 5B:
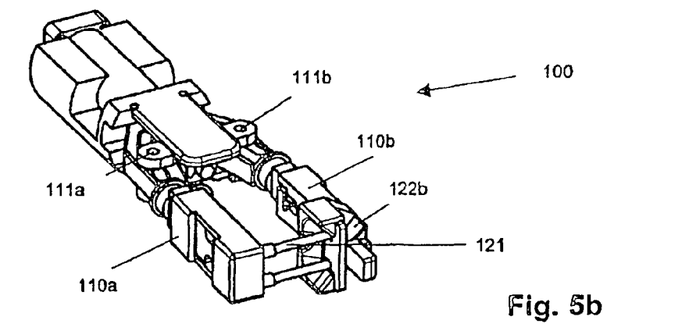
FIG. 5b an axonometric view of the end effector in a first closed state.
Figure 5C:
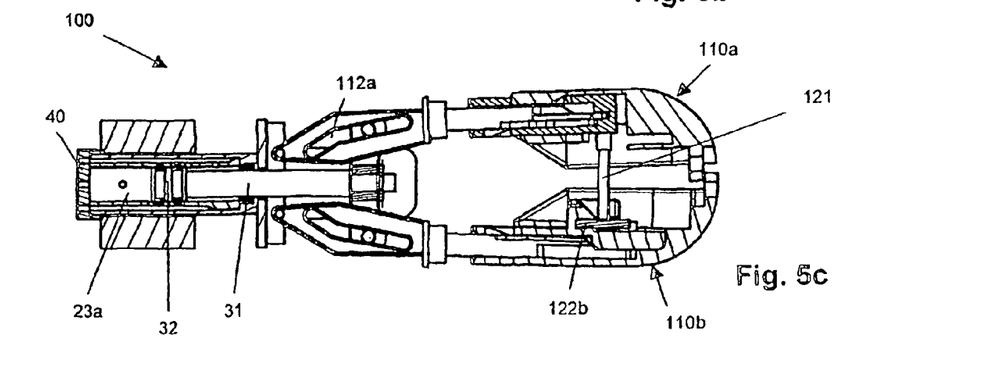
FIG. 5c a view from above of the end effector of FIG. 5b.

In FIGS. 5a to 5c the first closed state of the end effector 100, in which the preferably transoral placement of the end effector at the chosen site is carried out, is shown together with the corresponding hydraulic scheme. In this case the piston 30 is in an intermediate position within the cylinder 20 and partitions the cylinder interior into two cylinder spaces 23a and 23b. When the end effector 100 has been placed at the chosen site, for instance in the stomach, the two gripping elements 110a, 110b are moved to the opened position as in FIG. 4b.

Figure 6A:
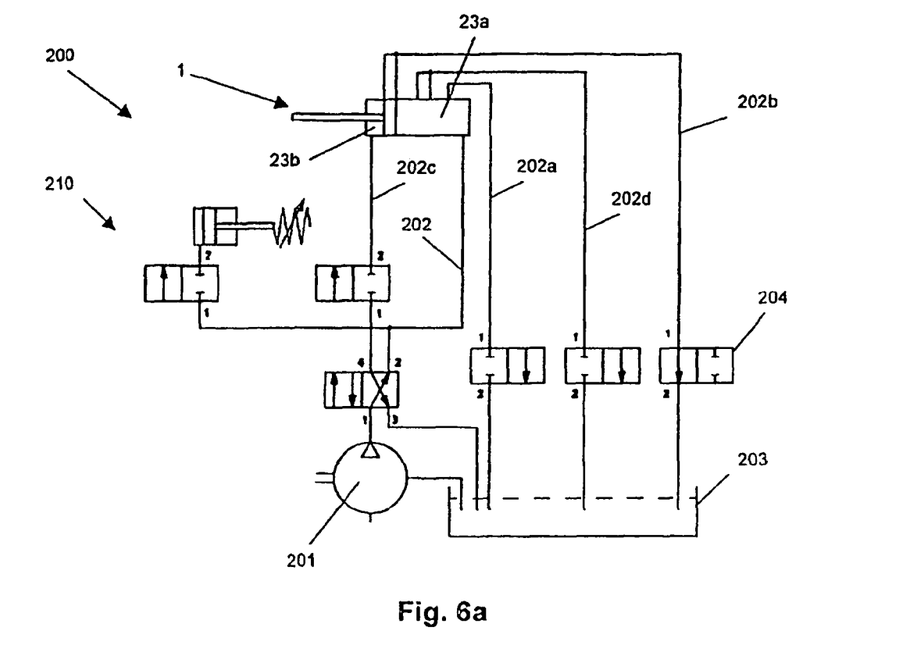
FIG. 6a a schematic hydraulic circuit for the end effector in a second closed state.
Figure 6B:
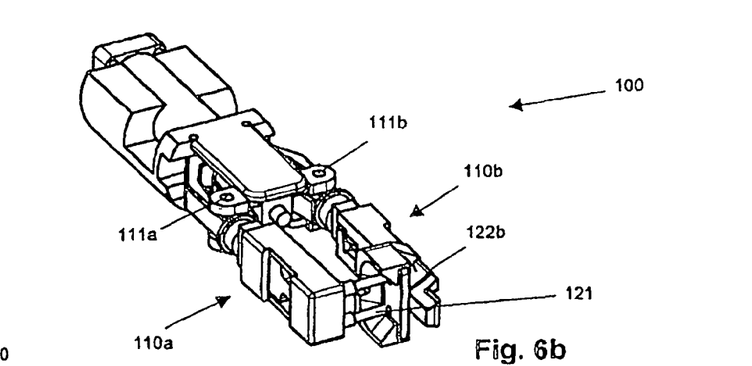
FIG. 6b an axonometric view of the end effector in a second closed state.
Figure 6C:
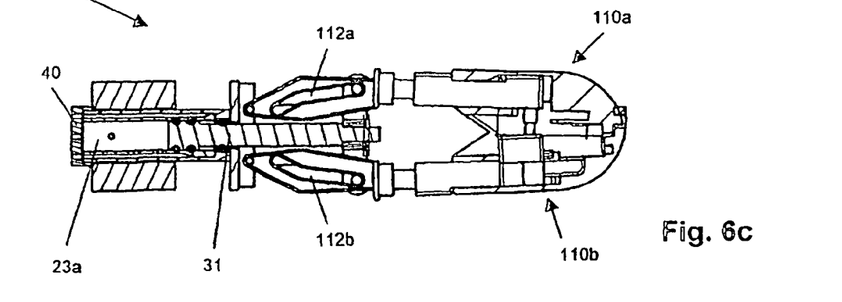
FIG. 6c a view from above of the end effector of FIG. 6b.
Figure 6D:
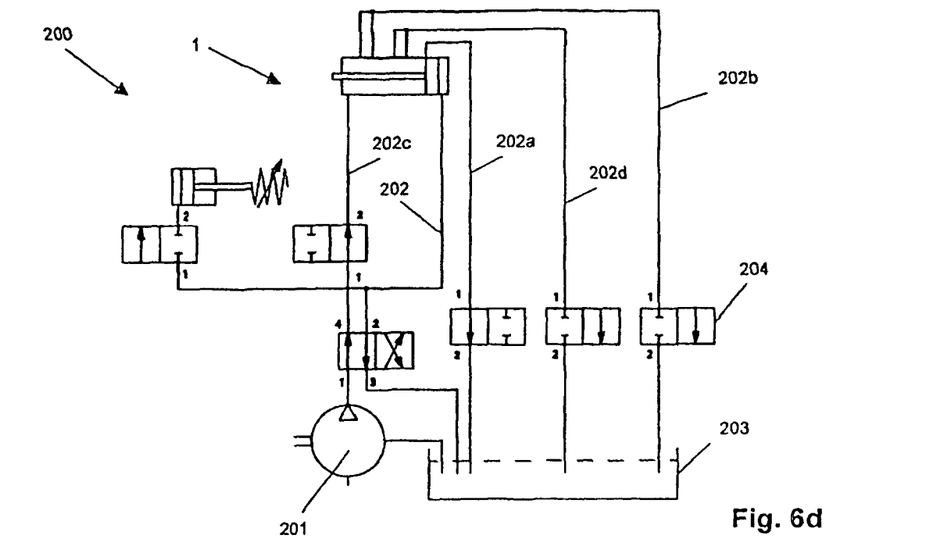
FIG. 6d a schematic hydraulic circuit for opening of the end effector from the second closed state.

By the subsequent closing of the gripping elements 110a, 110b the stomach tissue is gripped by the gripping elements 110a, 110b and penetrated by the pins 121. Finally, the piston 30 is moved to its uppermost position, as shown in FIGS. 6a to 6c, and the pins 121 of the staple device break at the predetermined breaking points (not shown).

After the end effector 100 has been opened by moving the piston 30 to its bottom position immediately adjacent to the sealing element 40 (FIG. 6d)—the hydraulic fluid flowing via the overflow passage 202d into the second cylinder space 23b,—the staple device remains in the tissue, and the end effector 100, again in the first closed position as in FIGS. 5b and 5c, may be retracted from the stomach through the oesophagus and the oral cavity.

It is obvious that use of the hydraulic actuating mechanism 1 of the invention is not limited to the depicted end effector 100, but that the hydraulic mechanism 1 may also be used with other end effectors, in particular for medical purposes, which conventionally are actuated by means of Bowden cables or other pulling or pushing elements.

Figure 7A:
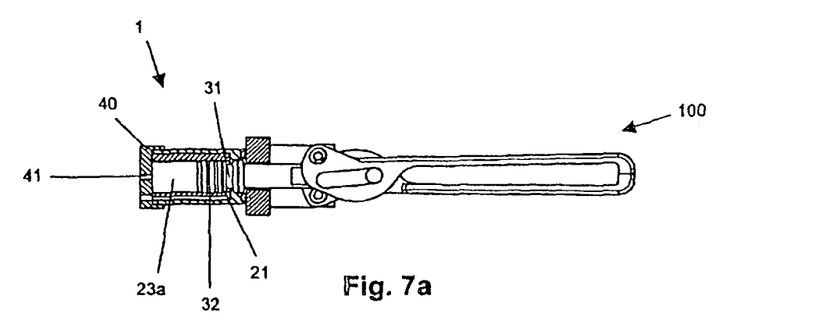
FIG. 7a a partial sectional view of another end effector.
Figure 7B:
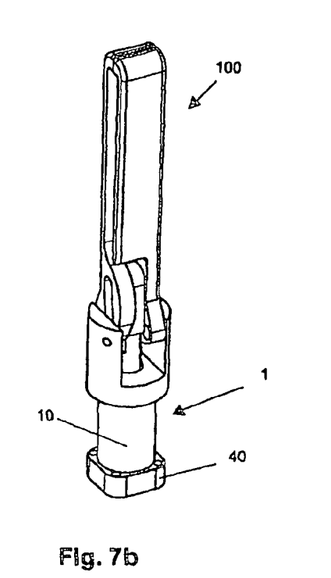
Figure 7C:
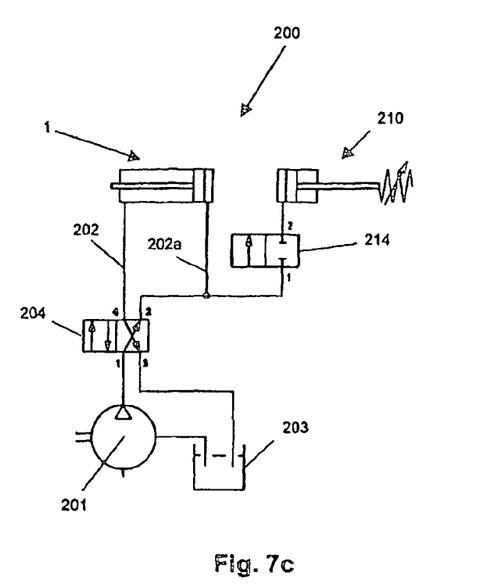

Pincer-like end effectors 100 for instance, as shown in FIGS. 7a and 7b, may also be operated with the actuating mechanism 1 of the invention. The hydraulic system 200 shown in FIG. 7c is somewhat simpler, since only two positions of the end effector, i.e., an open and a closed position, need to be controlled. For this reason the hydraulic actuating mechanism 1 is provided with only one overflow passage 21 in this variant, while the sealing element 40 has one hydraulic fitting 41 for pressure generation in the interior 23 of the cylinder 20 and one hydraulic fitting 41a which connects to the overflow passage 21. Of course, the hydraulic actuating mechanism as described above with more than one overflow passage could also be used.

In the dosed position of the pincer-like end effector 100 of FIGS. 7a and 7b the piston 30 is in the upper position. In order to open the pincer 100 the piston 30 is moved to its lower position by opening the overflow passage 21, such that the piston skirt 32 is immediately adjacent to the sealing element 40. Since this kind of end effector 100 is used especially during surgery to hold and/or fixate tissues over a prolonged period of time, the holding force of the end effector will deteriorate with the passing of time, especially so in mechanisms with Bowden cables, and in the worst case its grip on the tissues may be lost. Therefore an additional restoring element 210 is preferably provided, which by spring-action upholds the hydraulic pressure necessary for the correct functioning of the end effector 100.

Figure 8A:
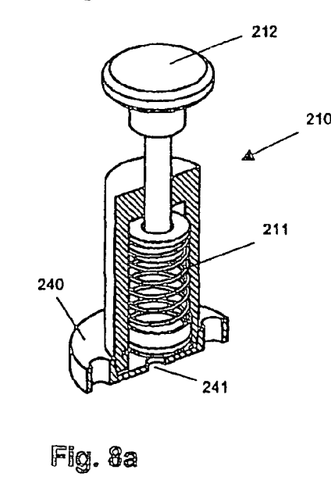
FIGS. 8a, 8b two partially cut views of a restoring device.
Figure 8B:
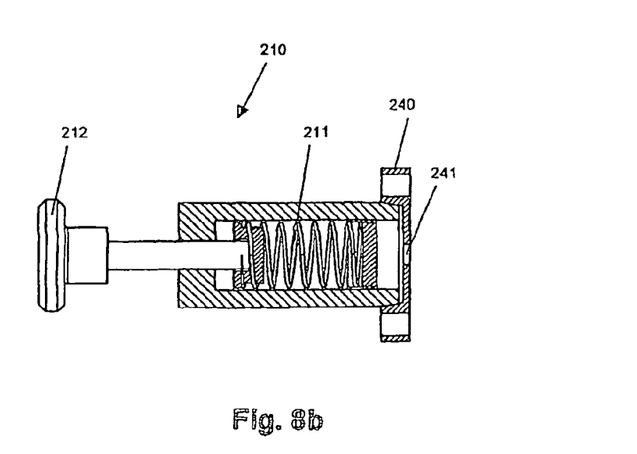

FIGS. 8a and 8b show a preferred variant of an additional restoring element 210. The restoring element 210 comprises a spring element 211, here a helical spring, and a turning knob 212, for adjusting the spring force to the desired level. Via a sealing plate 240 with a hydraulic fitting 241 the restoring element 210 is connected to the hydraulic system and may be activated by means of the switching element 214 (FIG. 7c), if required. It should be evident that this restoring element could also be used with diverse other kinds of end effector.

Additionally or as an alternative solution a signalling device may be provided, which signals a pressure drop within the hydraulic system 200, whereupon the restoring element 210 may be activated by the user.

Clearly, the invention is not restricted by the embodiments described here. In particular, the number and position of overflow passages can be adapted as required, more than five overflow passages being possible.

The invention claimed is:

1. A medical instrument comprising:
   an elongated element with an end effector positioned at one end of the elongated element, and
   a hydraulic actuating mechanism for operating the end effector,
   said hydraulic actuating mechanism including a cylinder with at least one overflow passage for a hydraulic fluid which is connected to an interior of the cylinder by at least one bore, and a piston movable within the cylinder along a longitudinal axis of the cylinder, said piston partitioning the interior of the cylinder into a first cylinder space and a second cylinder space, and connected via a piston rod to the end effector, and including at least one fitting for feeding hydraulic fluid into the first cylinder space and at least one further fitting which is connected to at least one overflow passage of the cylinder, and wherein the at least one overflow passage is formed as a groove on the exterior wall of the cylinder and is connected via the at least one bore to the interior of the cylinder, the cylinder being insertable into a sleeve.

2. The medical instrument according to claim 1, wherein the at least one bore of at least one overflow passage is located between an upper and a lower piston stop in such a way that the piston may be brought to at least one intermediate position in the cylinder which is situated between the upper and the lower piston stop.

3. The medical instrument according to claim 1, wherein the fittings for the hydraulic fluid, which are connected to the interior of the cylinder, are located in a sealing element placed at the end of the sleeve facing away from the piston rod.

4. The medical instrument according to claim 1, wherein the at least one overflow passage is located within the cylinder wall and is connected to the interior of the cylinder by at least one bore.

5. The medical instrument according to claim 1, including two bores for each overflow passage.

6. The medical instrument according to claim 1, wherein the end effector comprises two claw-like gripping elements, which can be moved towards each other from an opened position to at least one, closed position.

7. A device for actuating an end effector of a medical instrument according to claim 1, wherein a hydraulic system is provided, which cooperates with the hydraulic actuating mechanism of the medical instrument, said hydraulic system comprising at least one pump and at least one hydraulic line leading to each fitting of the sealing element, each hydraulic line preferably being provided with at least one switching element.

8. A method for hydraulically actuating an end effector of a medical instrument according to claim 1, wherein the position of the piston with piston rod within the cylinder is changed by hydraulic fluid flowing into the first cylinder space and/or flowing out of the second cylinder space via at least one overflow passage of the cylinder, the position of the piston determining the operational state of the end effector connected to the piston rod.

* * * * *